(12) United States Patent
Baumann et al.

(10) Patent No.: US 7,440,542 B2
(45) Date of Patent: Oct. 21, 2008

(54) METHOD AND MEASURING ARRANGEMENT FOR NONDESTRUCTIVE ANALYSIS OF AN EXAMINATION OBJECT BY MEANS OF X-RADIATION

(75) Inventors: Joachim Baumann, München (DE); Martin Engelhardt, München (DE); Jörg Freudenberger, Eckental (DE); Eckhard Hempel, Fürth (DE); Martin Hoheisel, Erlangen (DE); Thomas Mertelmeier, Erlangen (DE); Stefan Popescu, Erlangen (DE); Manfred Schuster, München (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/700,061

(22) Filed: Jan. 31, 2007

(65) Prior Publication Data

US 2007/0189449 A1 Aug. 16, 2007

(30) Foreign Application Priority Data

| Feb. 1, 2006 | (DE) | ......................... 10 2006 004 604 |
| Feb. 1, 2006 | (DE) | ......................... 10 2006 004 976 |
| Aug. 9, 2006 | (DE) | ......................... 10 2006 037 257 |

(51) Int. Cl.
*G01N 23/223* (2006.01)

(52) U.S. Cl. .......................................... 378/45; 378/44

(58) Field of Classification Search ............. 378/44–50, 378/62
See application file for complete search history.

(56) References Cited

U.S. PATENT DOCUMENTS

| 5,812,629 | A | 9/1998 | Clauser |
| 6,430,256 | B1* | 8/2002 | Yacoby ........................ 378/71 |
| 6,577,704 | B1 | 6/2003 | Holz |
| 6,859,516 | B2 | 2/2005 | Schneider et al. |

(Continued)

FOREIGN PATENT DOCUMENTS

EP 1 220 280 A2 7/2002

(Continued)

OTHER PUBLICATIONS

V.N. Ingal, E.A. Beliaevskaya: "X-ray plane-wave topography observation of the phase contrast from a non-crystalline object", J.Phys.D.: Appl.Phys., vol. 28, 1995. pp. 2314-2317.

(Continued)

*Primary Examiner*—Hoon Song
(74) *Attorney, Agent, or Firm*—Harness, Dickey & Pierce P.L.C.

(57) ABSTRACT

A method and a measuring arrangement are disclosed for nondestructive analysis of an examination object. In at least one embodiment of the method, x-radiation having a specific energy spectrum is generated by an x-ray source, with the aid of at least one x-ray/optical grating in the beam path of the x-radiation there is generated a standing wave field of this x-radiation that is positioned at least partially in the examination object, and the radiation excited by the x-ray standing wave field in the examination object is measured as a function of at least one relative position between the examination object and the x-ray standing wave field. Further, a material distribution in the examination object is inferred from the measurement result of the radiation excited by the x-ray standing wave field.

42 Claims, 2 Drawing Sheets

U.S. PATENT DOCUMENTS

| | | | |
|---|---|---|---|
| 2004/0081218 A1 | | 4/2004 | Tabirian et al. |
| 2005/0087699 A1* | | 4/2005 | Miyake .................. 250/492.1 |
| 2005/0228271 A1 | | 10/2005 | Diebold et al. |
| 2005/0264779 A1* | | 12/2005 | Hasegawa et al. ............. 355/53 |
| 2006/0290931 A1* | | 12/2006 | Zhao et al. .................. 356/369 |

FOREIGN PATENT DOCUMENTS

| | | |
|---|---|---|
| EP | 1 447 046 A1 | 8/2004 |
| JP | 62226048 A | 10/1987 |

OTHER PUBLICATIONS

U. Bonse, M. Hart: "An X-ray Interferometer", Applied Physics Letters, vol. 6, No. 8, Apr. 15, 1965, pp. 155-156.

T.Weitkamp et al.: "X-ray phase imaging with a grating interferometer", Optics Express, vol. 13, No. 16, Aug. 8, 2005, pp. 6296-6304.

M. Bavdaz, N. Gurker: "Coded Imaging X-Ray Microprobe", X-Ray Spectrometry, vol. 22, 1993, pp. 65-70.

Bergmann & Schäfer: "Lehrbuch der Experimentalphysik", Band 1 Mechanik, Akustik, Wärme (De Gruyter, Berlin), 1970, p. 554.

N. Chapman et al.: "Diffraction enhanced x-ray imaging", Phys. Med.Biol., vol. 42, 1997, pp. 2015-2025.

R. Fitzgerald: "Phase-sensitive X-Ray Imaging", Physics Today, vol. 53, Jul. 2000, pp. 23-26.

C.L. Koliopoulos: "Radial grating lateral shear heterodyne interferometer", Applied Optics, vol. 19, No. 9, May 1, 1980, pp. 1523-1528.

V. Lehmann: "The Physics of Macropore Formation in Low Doped n-Type Silicon", J.Electrochem. Soc., vol. 140, No. 10, Oct. 1993, pp. 2836-2843.

B.C. Platt, R. Shack: "History and Pinciples of Shack-Hartmann Wavefront Sensing", Journal of Refractive Surgery, vol. 17, Sep./Oct. 2001, pp. S573-S577.

J. Primot: "Theoretical description of Shack-Hartmann wave-front sensor", Optics Communications, vol. 222, 2003, pp. 81-92.

J. Primot et al.: "Deconvolution from wave-front sensing: a new technique for compensating turbulence-degraded images", J.Opt. Soc.Am.A,, vol. 7, No. 9, Sep. 1990, pp. 1598-1608.

J.Primot, L. Sogno: "Achromatic three-wave (or more) lateral shearing interferometer", J.Opt.Soc.Am.A., vol. 12, No. 12, Dec. 1995, pp. 2879-2685.

F. Roddier: "Variations on a Hartmann theme", Optical Engineering, vol. 29, No. 10, Oct. 1990, pp. 1239-1242.

R.V. Shack, B.C. Platt: "Production and Use of a Lenticular Hartmann Screen", J.Opt.Soc.Am., vol. 61, 1971, p. 656.

C.G. Schroer et al.: "Hard X-ray nanoprobe based on refractive x-ray lenses", Applied Physics Letters, vol. 87, 124103, 2005.

V. Ronchi: "Forty Years of History of a Grating Interferometer", Applied Optics, vol. 3, No. 4, Apr. 1964, pp. 437-451.

B.L. Henke: "Scattering Factors and Mass Absorption Coefficients", in: D.Vaughan (Editor) "X-Ray Data Booklet", 1988, Chapter 2.7, pp. 2-28-2-29.

S.W. Wilkins et al.: "Phase-contrast imaging using polychromatic hard X-rays", Letters to Nature, vol. 384, Nov. 28, 1996, pp. 335-338.

J.C. Wyant: "White Light Extended Source Shearing Interferometer", Applied Optics, vol. 13, No. 1, Jan. 1974, pp. 200-202.

Invention Report 2006 E02787 DE.

Introduction of Specification 200601959 and 2006 0 1153.

Gerlach, A.; Schreiber, F.: The X-ray Standing Wave Technique for the Investigation of Molecular Adsorbates on Surfaces—A Short Tutorial, 2004, S. 1-4.

Holotoyabko, E.; Quintana, J.P.: Control of synchrotron x-ray diffraction by means of standing acoustic waves. Review of Scientific Instruments, 2004, vol. 75, No. 3, S. 699-708.

Weitkamp, T: et al.: X-ray phase Imaging with a grating Interferometer. Optics Express, 2005, vol. 13, No. 16, S. 6296-6304.

* cited by examiner

METHOD AND MEASURING ARRANGEMENT FOR NONDESTRUCTIVE ANALYSIS OF AN EXAMINATION OBJECT BY MEANS OF X-RADIATION

PRIORITY STATEMENT

The present application hereby claims priority under 35 U.S.C. §119 on German patent application numbers DE 10 2006 004 604.8 filed Feb. 1, 2006, DE 10 2006 004 976.4 filed Feb. 1, 2006, and DE 10 2006 037 257.3 filed Aug. 9, 2006, the entire contents of each of which is hereby incorporated herein by reference.

FIELD

Embodiments of the invention generally relate to a method and/or a measuring arrangement for nondestructive analysis of an examination object by way of x-radiation, for example. More specifically, the examination object may be exposed to the x-radiation, and the radiation emitted thereupon by the object may be measured outside the beam path of the irradiating radiation.

BACKGROUND

It is known in x-ray radiography and x-ray tomography to determine the absorption coefficient $\mu(x, y, z)$ of an object in a precisely spatially resolved fashion, and to prepare an image of the object on the basis of this information. This imaging technique is based on the so-called absorption contrast. It is widely applied in medical diagnostics and in nondestructive testing in industry.

In the case of absorption contrast imaging, the various parts of the objects are weighted according to their mass absorption coefficient. A rough classification of the element concentration or of the tissue type of the object can be specified by evaluating the local absorption coefficient $\mu(x, y, z)$. In years gone by, the spatial resolution of this imaging has risen continuously and in the meantime pressed forward into the micrometer range.

It is known in x-ray radiography and x-ray tomography to alternately vary the tube voltage of a focus detector system during the scan, or to use focus detector systems arranged in an offset fashion and having different energy spectra, and thus to scan an object simultaneously with different radiation energies and to obtain projections with a set composed of dual energy data. A reconstruction based thereon then produces a base material decomposition in order to obtain pairs of images with material of high and low Z-value such as, for example, "bone" and "soft tissue".

This method enables an improved insight into the structure of an examination object, and is also of assistance, for example, in such applications as the bone densitometry of patients. It has also been proposed to extend this dual energy technique to a multiple energy technique that specifies the local absorption coefficient $\mu(x, y, z)$ for a number of photo-energies, and permits a finer differentiation. However, it is improbable that it actually achieves a spectral resolution as far as the separation of individual elements.

In addition to absorption, refraction itself is also suitable for x-ray imaging. In the case of so-called phase contrast imaging, the decrement $\delta$ of the complex refractive index $n=1-\delta-i\beta$ is determined in a spatially resolved fashion and reconstructed onto an image. In the case of phase contrast imaging, the various parts of the object are weighted using the gradient of that decrement $\delta$ in a fashion emphasizing the contours of the object. Various approaches to specifying phase contrast imaging experimentally have been undertaken in the past 40 years.

Various analytical methods have also been developed in materials analysis. These are, inter alia, x-ray fluorescence (XRF) analysis, electron beam microanalysis (EBMA), x-ray photoelectron spectroscopy (XPS), Auger electron spectroscopy (AES), secondary ion mass spectrometry (SIMS), infrared spectroscopy (IR), nuclear magnetic resonance (NMR) spectrometry, Raman spectroscopy (RS), x-ray diffraction (XRD) analysis, electron diffraction etc. Many of these methods have been developed in relation to local probes and spatially resolved analysis methods, and this can be used for scanning and/or imaging the objects, and thereby for preparing an image of the elemental distribution, of the distribution of molecular groups or compounds, of the distribution of crystalline phases or of the distribution of physical material properties of the object surface.

In most cases, however, 3D analyses are hampered by the fact that either the information depths are too small, or appropriate optics for imaging element-specific signals are not available. The latter holds especially for signals with a large penetration depth such as x-radiation and gamma radiation.

There is therefore the continuing problem of finding a method and a measuring arrangement with the aid of which it is possible to determine the elemental and/or molecular distribution in the interior of an examination object in a nondestructive fashion.

SUMMARY

In at least one embodiment of the invention, a novel method and/or a novel measuring arrangement is disclosed for nondestructive analysis of an examination object with reference to its elemental and/or molecular distribution with the aid of x-radiation.

In the case of the known x-ray analysis methods, mostly x-rays with specific properties—intensity, energy and direction—are guided through an examination object and their change in properties is measured after passage through the examination object.

The inventors have recognized, in at least one embodiment, that a spatial analysis of an examination object with the aid of x-radiation is also possible when the x-radiation that penetrates as probe into the examination object is influenced upstream of the object in such a way that an intensity distribution that is spatially known and can be influenced comes into being such that the specific effects of this radiation on different elemental and/or molecular distributions in the object can be measured outside the examination object.

Thus, in concrete terms, there is generated with the aid of an x-ray/optical grating in the beam path of the x-radiation a standing wave field into which the surface or the interior of the examination object is brought such that periodically spaced locations of strong and weak x-ray intensity are produced whose effect outside the examination object can be detected, it being possible at least to make statements relating to the spatial distribution of specific structures in the examination object by means of relative positioning of the standing wave field relative to the examination object. A display of the elemental or molecular concentration can be obtained by the application of computing operations such as, for example, Fourier transformation of the measured value profile that is produced by relative displacement of sample and standing wave field.

Thus, use is made of a grating in the beam path upstream of the examination object that acts as a diffracting grating and splits the primary beam from an x-ray source into beams of +1st and −1st order and the beam of 0th order (=direct/penetrating beam) and beams of higher order. The diffracted beams of +1st and −1st order interfere with one another in the wave field downstream of the grating and form a standing wave field with a well defined spatial frequency.

A suitable photon energy E or wavelength λ must be selected in order to ensure the required penetration through the object. This selection can be done in accordance with known radiological tables in the case of an object of approximately known dimension, density and average matrix composition.

The diffraction and 2Θ of the grating is described by Bragg's law:

$$\Theta = \arcsin\frac{\lambda}{2g_1},$$

$g_1$ being the period of the x-ray/optical grating $G_1$, and λ the wavelength of the x-radiation.

A standing wave field is therefore formed downstream of the grating along the optical axis. This standing wave field has a transverse and a longitudinal periodicity. In the case of a parallel beam, the transverse period $g_2$ of the standing wave generated is half the period $g_1$ of the grating, and so it holds that:

$$g_2 = \frac{1}{2}g_1.$$

Standing waves are also produced along the optical axis. Their periodicity is differently expressed. The shortest distance $d_1$ at which the contrast of the interference strips, that is to say the standing wave field, exhibits a maximum is a function of the wavelength and the grating period $g_1$, and is given by:

$$d_1 = \frac{1}{2}\frac{g_1^2}{4\lambda}.$$

The variable $d_1$ is denoted as the 1st Talbot distance.

Further maxima occur at the mth Talbot distance and $$d_m = \left(m - \frac{1}{2}\right)\frac{g_1^2}{4\lambda}.$$

A diffraction is observed at each grating that is penetrated by the x-radiation, but in order to obtain a standing wave field the arrangement must fulfill specific coherence requirements. To this end, the spatial coherence length of the radiation emanating from the source must be greater than or of the same order of magnitude as the period of the grating $g_1$. In the case of a source grating distance $r_1$ and a source size s in the transverse direction, this means that:

$$g_1 \leq \lambda \frac{r_1}{s}.$$

It is possible in principle to select each period that corresponds to the abovementioned requirements, but a value of one to several μm for the period is preferred because of the limitations of the production method.

It merely pointed out that the equations exhibited above relate to a parallel geometry of the radiation. When use is made of fan geometry, there is a need for appropriate geometric adaptation of the equations.

Any desired grating can be used as beam splitter for the purpose of at least one embodiment of the invention. Such gratings can be phase gratings or amplitude/absorption gratings, mixed forms of the two or else crystal gratings. However, it is particularly advantageous to design them as phase gratings with a phase jump of π, since here the incident radiation intensity is virtually completely diffracted into the +1st and −1st diffraction order. In order to obtain a phase jump of π or λ/2 for the resonance energy E corresponding to the wavelength λ, that is to say in order to achieve a maximum intensity in the diffraction order of +1st and −1st order, it is necessary to calculate the height $h_1$ of the webs of the phase grating $G_1$ with the aid of the following formula:

$$h_1 = \frac{\lambda}{2\delta},$$

δ being the real decrement of the refractive index of the grating material. For x-rays, the refractive index n can be described as $$n = 1 - \delta - i\beta,$$

β being the imaginary decrement, which is related to the absorption, δ being the real decrement, which is related to the refraction. The energy selectivity of the phase grating can be used to select the desired photon energy. However, it is to be noted that the energy bandwidth of a phase grating is relatively wide at +/−5%, and this leads to a relatively high intensity when use is made of x-ray tubes.

Gratings made from aluminum, silicon, diamond or plastics are proposed for low photon energies. It is preferred to propose gratings made from chromium, nickel, molybdenum, tantalum, tungsten, platinum, gold, lead or uranium or compounds of these elements for high photon energies. In the case of the latter materials, the required phase jump of π can be achieved with smaller grating web heights that can be more easily produced and which do not excessively collimate the beams.

It may also be pointed out in principle that, because of the maximum achievable web height of a grating, or because of the alignment of the grating webs on a fan-shaped or conical beam path, it can also be advantageous to arrange a number of phase or absorption gratings sequentially in order to avoid shading effects. In this case, in accordance with the beam spreading used it is also possible as a consequence for the gratings to exhibit different grating periods and/or inclined grating webs, such that the grating gaps and grating webs are aligned and/or run as parallel as possible to the beam direction.

Moreover, when use is made of a phase grating it is also on occasion additionally advantageous to fill the grating gaps with a material of higher absorption than the material of the grating. It is, however, particularly favorable in this case when the filling of the grating gaps of all or one grating is fashioned in such a way that the radiation intensity downstream of the grating is the same irrespective of whether the radiation intensity is measured downstream of the grating webs or downstream of the grating gaps with the filling material. The character of the interference pattern is thereby optimized.

The period of the grating should preferably have a width ratio of grating gaps to grating webs of 1:1 in order to obtain the highest intensity of the diffraction order +1 and −1.

In principle, the profile of the grating can be rectangular, but according to at least one embodiment of the invention, use can also be made of other profile shapes that influence the distribution of the intensities over the various diffraction orders. Given a rectangular grating profile, the intensity of the diffraction order +1 and −1 is approximately 85% of the primary beam. The residue resides in this case in higher diffraction orders and the penetrating direct beam of 0th order.

As already mentioned, other types of gratings than phase gratings can also generate standing waves. For example, amplitude gratings can be used that produce a periodicity through a sequence of materials of different absorption. Moreover, not only "artificial" gratings can be applied for the purpose of the invention, but also other diffracting devices such as, for example, monocrystals or a number of layers that are inserted between the radiation source and the examination object.

Such a resulting external standing wave field has a sinusoidal intensity distribution. It is used for the purpose of "exciting" the atoms of the objects selectively at those positions where the standing wave field exhibits its antinodes. The atoms can in this case absorb an x-ray photon and use its energy to ionize an inner shell. This process is then associated with the emission of a photoelectron.

In the next step, the ionized inner shells can relax through two alternative reaction channels. Either an x-ray photon is emitted (x-ray fluorescence radiation), or an Auger electron is emitted. One or more of the three emitted characteristic probe/radiations can be used to detect the excitation of the atoms. Each probe constitutes an element-specific signal or an element-specific radiation that can be measured by appropriate detectors.

For example, solid state detectors such as, for example, Si(Li) detectors, high purity Ge detectors, Si-PIN detectors or Si-drift detectors can be used with particular advantage for emitted x-ray fluorescence radiation. When the object to be examined is very small, it is also possible to use wavelength-dispersive spectrometers such as are known from electron beam microprobes. By way of example, cylindrical mirror analyzers, hemispherical analyzers, 127° analyzers or opposing field analyzers are proposed for use in analyzing photoelectrons and Auger electrons.

In order to determine the elemental concentration distribution, the object can be moved in a number of steps by fractions of a period. The intensity of the element-specific signals can be measured with one of the above described detectors. When the elemental distribution in the object is not homogeneous, a sinusoidal intensity profile is produced in each case as a function of the position in the standing wave field. Phase, amplitude and mean value of the element-specific signal can be determined therefrom in this case.

The complex Fourier amplitude, or the amplitude shift and phase shift that corresponds to the period or spatial frequency of the standing wave field can thus be calculated by Fourier analysis. When the elemental distribution in the object is periodic and has one and the same period as the standing wave field, this can be used to describe completely a Fourier amplitude of the concentration profile of the elements in the object. However, this will not be the case in most instances.

In order to obtain the elemental distribution in the general case, it is necessary to determine a number of different Fourier amplitudes, and for the ideal description of the elemental distribution the Fourier amplitudes of all the spatial frequencies that are included in the object should be determined. In this case, the lowest spatial frequency corresponds to the reciprocal of twice the dimension of the object, while the highest spatial frequency corresponds to the reciprocal of the smallest interatomic distance. The analysis can be restricted to portions of the maximum spatial frequency range, depending on the aim of the examination. It is possible to impose a restriction to testing one or a few spatial frequencies whenever the aim is to test the observance of specific stipulations within the framework of a nondestructive quality test.

By way of example, the variation in the spatial frequency of the exciting standing wave field can be achieved in the following way:

(i) in a parallel beam by varying the grating with the use of a, preferably automatic, grating changer, (ii) with the use of the Moire pattern, resulting from two gratings that are rotated relative to one another, as settable grating, or (iii) with the use of a grating of variable standing wave period on the basis of a sound/ultrasound standing wave pattern whose period and spatial frequency are controlled by the frequency of the connected ultrasound generator, (iv) in fan geometry or conical beam geometry the period varies with the distance from the phase grating.

In addition to the transverse period addressed in (i) to (iv), the standing wave field also has a very much larger longitudinal period that can likewise be used to scan the examination object. The longitudinal period can also be influenced in the following way:

(v) a change in the wavelength via (a) upstream monochromators, or (b) a variation in the resonance energy via the web height in the case of the rigid grating, or via the ultrasound amplitude in the variable grating.

A variation in the primary energy is not mandatory in this method. However, the period of the interference pattern, that is to say the scanning spatial frequency, can be tuned in a wide range. The following steps can be carried out to this end: (i) variation of the primary energy in accordance with a λ dependence of the Talbot distance, (ii) variable grating (for example: gas cell+ultrasound), (iii) two rotated gratings for forming a rotation Moires, (iv) a large set of gratings of different period, (v) rotating the object and using the difference from lateral to longitudinal interference pattern period.

The acoustic standing waves that serve as diffraction gratings for x-rays could be standing waves in a cell filled with gas. In the event of operation as phase gratings, in order to obtain a sufficient phase shift, at best a phase jump of π, use should be made of pressurized gas and/or gas at high density, for example: $SF_6$, $WF_6$. It is also possible to make use as diffraction gratings for x-rays, of waves in liquids or surface acoustic waves in solid material, for example piezomaterial, PZT, $LiNbO_3$, LiTaO3, or quartz.

As described at the beginning, it is possible to produce an x-ray standing wave field with a specific transverse period (transverse spatial frequency) and a specific longitudinal period (longitudinal spatial frequency). No standing waves are produced in this case perpendicular to the grating diffraction plane. The field extends in this direction virtually homogeneously within defined slits of a parallel beam or a fan beam.

It is proposed to carry out at least one embodiment of the abovementioned procedure in the direction along the optical axis in order to determine the elemental distribution along the optical axis. In order to determine the elemental distribution transverse to the optical axis, that is to say in the diffraction plane, it is proposed to carry out this scanning procedure in the direction transverse to the optical axis, that is to say in the diffraction plane. Furthermore, information relating to the elemental distribution on the other transverse axis can be obtained when the grating is rotated by 90° about the optical axis (=beam direction of the radiation irradiating the examination object), and the scan is carried out in this transverse direction to the optical axis, that is to say in the diffraction plane. It is also possible to rotate the object as an alternative to rotating the grating.

Instead of using a line grating, and measuring in two grating orientations (0° and 90°), it is also possible according to at least one embodiment of the invention to use a Hartmann mask, preferably with a chessboard pattern, preferably designed as a phase grating. This has the advantage that the Fourier components can be simultaneously determined in the two transverse directions.

When the Fourier amplitudes $A_{j\overline{H}}$ are determined in all three spatial directions, the spatially dependent elemental concentration distribution $A_j(\overline{r})$ of the elements j can be synthesized by way of:

$$A_j(\overline{r}) = \sum_j A_{j\overline{H}} \exp(-i\overline{H} \cdot \overline{r}),$$

in which $\overline{H}$ is the vector $\overline{H}=(H_x,H_y,H_z)$ consisting of the spatial frequency components in the three spatial directions. The position at which the elemental distribution is viewed is described by the spatial vector $\overline{r}=(x,y,z)$.

It is possible in this way to analyze the 3D concentration distribution of all the elements of the period, system. If the aim is to determine the elemental concentration distribution only in one dimension or in two dimensions, the formal approach is the same, it being possible to omit the direction or the directions that are of no interest.

Within the framework of at least one embodiment of the invention, it is also possible to use a fan beam geometry or conical beam geometry instead of a parallel beam geometry. The fan beam geometry or conical beam geometry generally also has a correspondingly formed standing wave field as a consequence. This fan-shaped or conical standing wave field has a transverse period that increases along the optical axis in the propagation direction. This property of standing waves in fan/conical beam geometries can be used to determine the Fourier amplitudes transverse to the optical axis for the various spatial frequencies with the aid of a single grating design, it being only the position of the object along the optical axis that is varied. In addition to the enlargement effect, there is a need to take account of the—somewhat more long wave—intensity modulation corresponding to the Talbot distance in the case of variation in the position of the object along the optical axis downstream of the grating.

Reference may also be made by way of clarification to the following relationships:

the emission of x-ray photons from laboratory x-ray sources (x-ray tubes, secondary targets, plasma sources, radioactive sources, parametric x-ray sources, channeling radiation) as well as from conventional synchrotron radiation sources of first to third generation is subject to stochastic processes. The emitted x-radiation therefore has no spatial coherence as such. However, in phase contrast radiography and phase contrast tomography and/or in any desired interference experiment the radiation of x-ray sources behaves like spatially coherent radiation when the viewing angle at which the source appears to the viewer of the object, the grating or the detector is sufficiently small. The so-called (lateral) coherence length L may be specified as a measure of the spatial coherence of an extended x-ray source:

$$L = \lambda \frac{a}{s}.$$

Here, $\lambda$ is the wavelength, s the transverse size of the source, and a the source/viewer distance. Some authors also denote half of the above defined value as the spatial coherence length. The exact value is of a secondary nature; what is important is that the coherence length L be large in comparison to the (lateral) dimension of the spatial region from which beams are to interfere with one another.

For the purpose of the patent application, coherent radiation is to be understood as a radiation that leads to the formation of an interference pattern under the given geometries and distances for the desired x-ray/optical grating. It goes without saying that the spatial coherence, and thus the spatial coherence length, are always determined by the three variables of wavelength, size of source and viewing distance. In the interest of a compact formulation, this state of affairs has been shortened to terms such as "coherent x-radiation", "coherent x-ray source" or "point source for generating a coherent x-radiation".

These abbreviations are based on the fact that the wavelength or the energy E of the x-radiation is limited in the applications discussed here by the desired penetrating power of the examination object, on the one hand, and the spectrum available in the case of laboratory x-ray sources, on the other hand. The distance a between source and viewer is also subject to limitations in laboratory set ups for nondestructive materials testing or medical diagnostics. Thus, it is the size of the source s that mostly remains as the last degree of freedom, even when narrow limits are set here by the relationships between the size of the source and tube power.

The source grating permits the use of larger, and thus more powerful x-ray sources. The narrow slits of the source grating ensure that all the beams that emerge from one and the same slit observe the required spatial coherence. Only photons from one slit can interfere with one another, that is to say be superposed in the correct phase relation. It is true that no in-phase superposition is possible between the photons from slit to slit of the source grating, but at least one superposition, correct in terms of intensity, of the wave antinodes and the wave nodes of the standing wave field is possible giving a suitable tuning of the source grating period $g_0$ and the interference pattern period $g_2$ as well as of the distance l between the source grating $G_0$ and phase grating $G_1$, and the distance d between the phase grating $G_1$ and interference pattern $G_2$ in accordance with $g_0/g_2=l/d$. In the shortened formulation of the patent application, use is made in this context of the term "quasi-coherent radiation", or "quasi-coherent radiation source".

The temporal or longitudinal coherence of the radiation goes along with the monochromaticity of the x-radiation or the x-ray source. The x-radiation of intensive characteristic lines mostly has an adequate monochromaticity or temporal coherence length for the applications discussed here. It is also possible for a sufficiently narrow spectral region to be filtered out from a bremsstrahlung spectrum or synchrotron spectrum, and thus for the requirements placed on the temporal coherence length in the present arrangements to be fulfilled by using upstream monochromators or by selecting the resonance energy through the web height of the phase grating.

In accordance with the above described idea of at least one embodiment of the invention, the inventors propose in a first concrete design a method for nondestructive analysis of an examination object that has at least the following method steps:

- x-radiation having a specific energy spectrum is generated by an x-ray source,
- with the aid of at least one x-ray/optical grating in the beam path of the x-radiation, there is generated a standing wave field of this x-radiation that is positioned at least partially in the examination object, and
- the radiation excited by the x-ray standing wave field in the examination object is measured as a function of at least one relative position between the examination object and the x-ray standing wave field, a material distribution in the examination object being inferred from the measurement result of the radiation excited by the x-ray standing wave field.

According to at least one embodiment of the invention, any desired x-ray/optical grating can be used as beam splitter. Such gratings can be phase gratings or amplitude/absorption gratings, mixed forms of the two or else crystal gratings. However, it is particularly advantageous to design the phase grating with a phase jump of $\pi$, since here the incident radiation intensity is virtually completely diffracted into the +1st and −1st diffraction order.

The total intensity of the radiation excited by the x-ray standing wave field can be measured as a function of the relative position between examination object and x-ray standing wave field, the amplitude, the phase and the mean value of the excited radiation intensity with regard to the spatial frequency prescribed by the specific standing wave field can be determined from the intensity profile. This is preferably performed by a Fourier analysis of the intensity profile.

Instead of the total intensity, it is correspondingly also possible to measure the spectral intensity distribution at least with reference to two energy regions as a function of the relative position between the examination object and x-ray standing wave field.

The spatial distribution of at least one specific material in the examination object can be determined from the results of a number of Fourier analyses.

In order to produce different relative positions between the x-ray standing wave field and the examination object, and to measure the excited radiation, the x-ray/optical grating can be positioned differently relative to the examination object, or it is possible to use different x-ray/optical gratings with a different grating period that are inserted alternately for the purpose of measurement into the beam path.

A further example variant for producing different relative positions consists in using an x-ray/optical grating produced by ultrasound, standing waves of different period also being formed in this grating.

What is important with all these variations relating to the relative positioning or relative displacement of the standing wave field in the examination object is that the maxima and minima of the standing wave field occur at different positions in the examination object, and so information relating to the spatial material distribution in the examination object can be gathered from the radiation emissions respectively generated and measured at other locations.

By way of supplement, there is also the possibility of carrying out the described method with different energies of the exciting x-radiation. It is possible to this end, for example, to use at least one phase grating in the beam path that can be tuned to the radiation energy, the tuning of the phase grating being set for each currently used radiation energy. It is thereby possible when using the brems spectrum, for example, to "tune" over the entire spectrum, or when use is made of a spectrum having a number of characteristic lines it is possible for these lines to be used specifically without rebuilding the measuring arrangement.

A standing ultrasound field in a medium can be generated as settable phase grating, and structural differences in this medium can thereby be produced that correspond to a phase grating in alignment and grating period. A gas can preferably by used as medium, since it is possible here for the ultrasound field to produce particularly high density differences. However, it is also possible to use a liquid, a suspension or a solid, preferably a piezoelectrically excitable solid.

An x-ray tube with a punctiform focus, or synchrotron radiation can be used as radiation source of the coherent x-radiation. The focus of laboratory radiation sources is, for example, frequently too large for the required coherence length, or the intensity of micro focus sources is too small. A source grating can be of assistance here. If, for example, a higher radiation intensity is required, it is then also possible to use radiation source as an x-ray tube having at least one absorption grating (=source grating), arranged in the beam path downstream of the focus, in order to generate a field of quasi-coherent x-rays with a specific radiation energy. Another possibility resides in forming the focus such that radiation with a grating-like spatial distribution emanates from it. Such source gratings or foci are also proposed for phase contrast computed tomography.

In order to determine the secondary or scattered radiation emitted by the standing wave field of the examination object, it is possible to use at least one detector that can preferably also be designed as an energy-resolving detector such that the spectral distribution of the radiation emitted by the standing wave field in the examination object can be determined. According to at least one embodiment of the invention, the x-ray emission and/or electron emission excited by the x-ray standing field can be determined here.

In accordance with at least one embodiment of the inventive method, it is alternatively proposed that the radiation emitted by the standing wave field in the examination object be measured as a function of the relative position with reference to one direction, that is to say one dimensionally, or in a plane, that is to say two dimensionally, or else three dimensionally. In most cases, a corresponding relative position between the standing wave field and the object is also brought about in accordance with the measured dimension, although it is also possible at the same time to measure a plane, that is to say two dimensions, by using a so-called Hartmann grating.

The relative positioning between the examination object and standing wave field can, for example, be implemented by a movement of the examination object or by a movement of the phase grating, at least through its grating lines.

In accordance with the previously outlined inventive method, the inventors also propose, in at least one embodiment, a measuring arrangement for nondestructive analysis of an examination object that has at least the following features:

- an x-ray source for generating coherent or quasi-coherent x-radiation having at least one specific radiation energy,
- at least one x-ray/optical grating that is arranged in the beam path of the x-ray source and generates a x-ray standing wave field that is partially positioned in the examination object, and
- at least one detector that is positioned outside the beam path of the x-ray source and which measures the radiation emitted by the standing wave field of the examination object as a function of the relative position between the examination object and the standing wave field with reference to their intensity and energy distribution.

Proposed in addition for controlling the measuring arrangement and evaluating the measurement results is an arithmetic and control unit that contains programs that execute during operation the method steps of the previously described inventive measuring and evaluation method.

In at least one embodiment of the inventive analysis apparatus, the x-ray/optical grating can be designed as a phase grating for at least one specific radiation energy that is used. It is advantageous in this case when at least one grating that can be variably tuned to the radiation energy is provided in the beam path. Such a variably settable grating can have at least one ultrasound generator and in each case an opposing ultrasound reflector or a further ultrasound generator such that a standing ultrasound field is thereby generated and there are produced in a medium structural differences that correspond to an absorption grating or phase grating in alignment, grating period, absorption behavior and phase behavior.

A gas can preferably serve as the medium of such an ultrasound generated grating. However, also possible alternatively is the use of media such as a liquid, a suspension or a solid, a piezoelement that can be excited to vibrate electrically being preferred as solid.

It is proposed, furthermore, to make use as radiation source of an x-ray tube with a punctiform focus, or a synchrotron. Another alternative for generating quasi-coherent radiation resides in making use as radiation source of an x-ray tube with at least one absorption grating (=source grating) arranged in the beam path downstream of the focus.

At least one, preferably an energy-resolving, detector can be arranged with reference to the measurement of the radiation emitted by the examination object through the standing wave field.

In order to position the examination object relatively with reference to the standing wave field, it is possible to provide controllable drive device(s) that enable relative positioning in one to three dimensions. For example, this may be piezoelements that move the examination object or the grating, or it is also possible to use an apparatus for moving the grating lines as means for producing the desired relative position. In the case of the use of a grating produced by ultrasonic waves, such an apparatus comprises an appropriate control of the ultrasound generator that generates the standing wave field such that the wave maxima and wave minima are manifested at different sites.

BRIEF DESCRIPTION OF THE DRAWINGS

The embodiments of the invention are explained in more detail below with the aid of the figures, only the features required to understand the invention being illustrated, and the following reference symbols being used: 1: x-radiation; 2: gratings; 2.1: webs; 2.2: gaps; 3: diffracted x-radiation; 4: standing wave field; 5: examination objects; 5.x: different materials in the examination object; 6: x-ray fluorescence radiation; 6.x: x-ray fluorescence radiation of different character; 7: detector; 8.1: intensity profile; 8.2: amplitude; 8.3: mean value; 8.4: phase; 9: anode; 10: apparatus for electron beam deflection; 11: control and arithmetic unit; 12: memory; 13.x: control and data line; 14: movement apparatus; 15: object holder; 16: ultrasound generator; 17: ultrasound reflector; 18: strip-shaped focal spot; 19.1.1, 19.1.2: movements of the examination direction; 19.2.1, 19.2.2: movements of the grating; 19.3: movement direction of the electron strip on the anode; 20: gas cell; I: intensity.

In detail.

DETAILED DESCRIPTION OF THE EXAMPLE EMBODIMENTS

Figure 1:
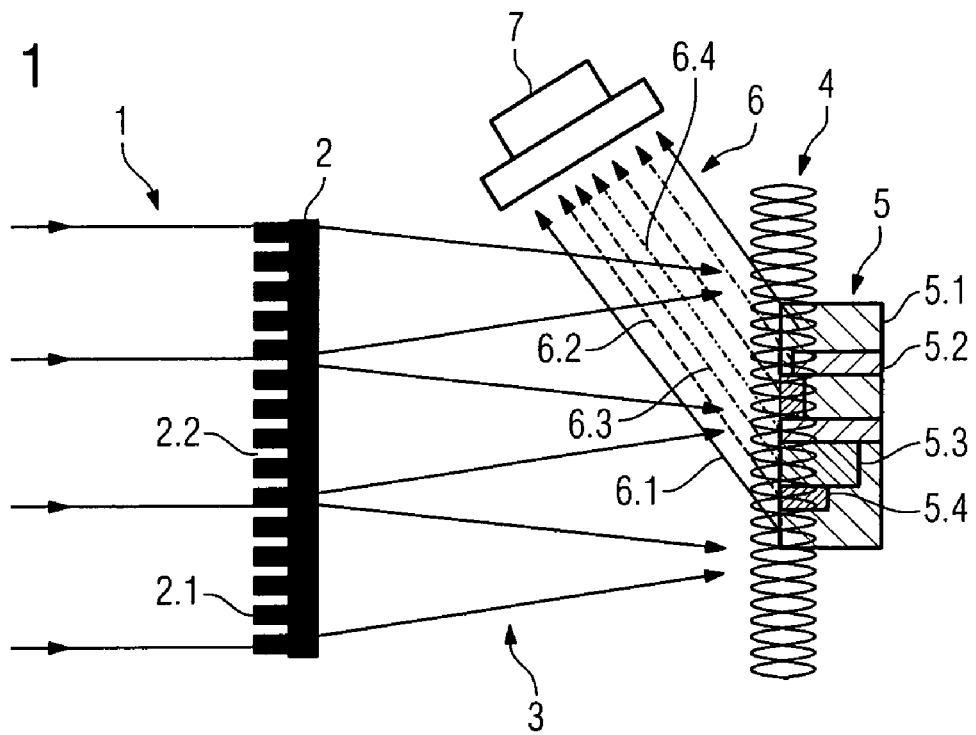
FIG. 1 shows an inventive measuring arrangement for non-destructive analysis of an examination object by way of x-radiation.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows an inventive measuring arrangement including an absorption or phase grating 2 with webs 2.1 and gaps 2.2 that builds up a standing wave field 4 from a penetrating x-radiation, the standing wave field 4 being positioned in an examination object 5, and generating radiation, preferably x-ray fluorescence radiation 6, in this examination object 5 as a function of the distribution of the elements, which are measured via a detector 7.

In the illustration shown in FIG. 1, coherent or quasi-coherent x-radiation 1 emanating from an x-ray source (not illustrated here) comes from the left and strikes the x-ray/optical grating 2, in which there is generated a diffracted x-radiation 3 and, therefrom, the standing wave field 4 that substantially corresponds in its planar extent to the planar extent of the generating absorption or phase grating 2. In the illustration shown, an examination object 5 with differing materials 5.1 to 5.4 is arranged in this standing wave field 4.

Owing to the structured formation of the examination object 5, radiation 6 of different character 6.1 to 6.5 that varies as a function of the relative position of the examination object 5 from the standing wave field 4 is received in the detector 7 as a function of the elemental distribution and as a function of the position of the standing x-ray wave 4 relative to the examination object 5.

Figure 2:
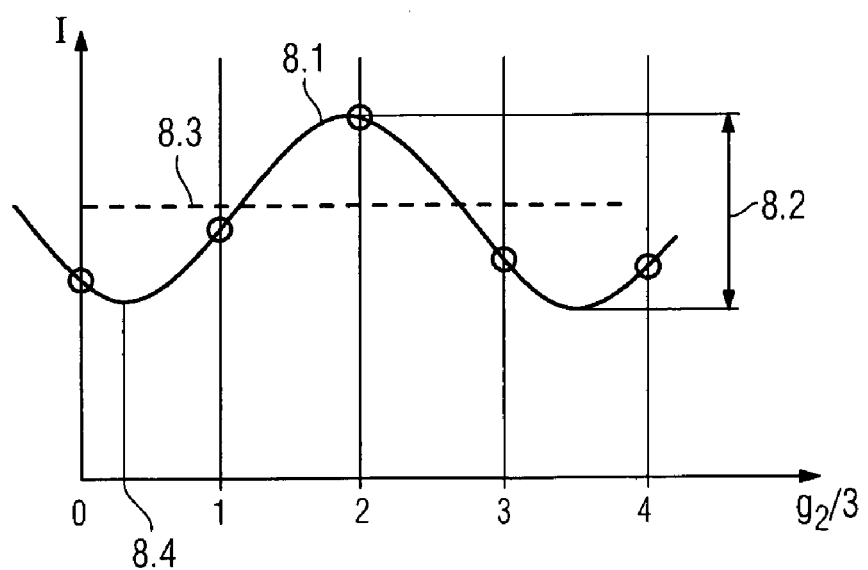
FIG. 2 shows a schematic measurement curve of one of the emitted radiations of a standing wave from an examination object.

If a specific radiation emitted by the examination object for example the type in accordance with reference symbol 6.2, is plotted with the aid of the detector 7 as a function of the relative position of the examination object 5 from the standing wave field 4, the result is an intensity profile such as is demonstrated by way of example in FIG. 2. Here, the intensity I of a signal is shown against the relative position, plotted on the abscissa, between examination object and x-ray standing field, the relative position being plotted in units of $g_2/4$, where $g_2$ is the respective period of the standing wave field currently being used.

If the change in intensity of a specific emitted radiation is now directly shown/plotted in relation to the relative position between standing wave field and the examination object or determined via a number of measuring points depicted as circles, the result is the intensity profile 8.1. The amplitude 8.2, the phase 8.4 and the mean value 8.3 can be determined therefrom. By measuring these variables over a multiplicity of standing wave fields of different periods inside the examination object, and a multiplicity of movement directions of the examination object relative to the standing waves, it is possible via an appropriate Fourier analysis to determine the elemental distribution in an examination object in one to three dimensions.

Figure 3:
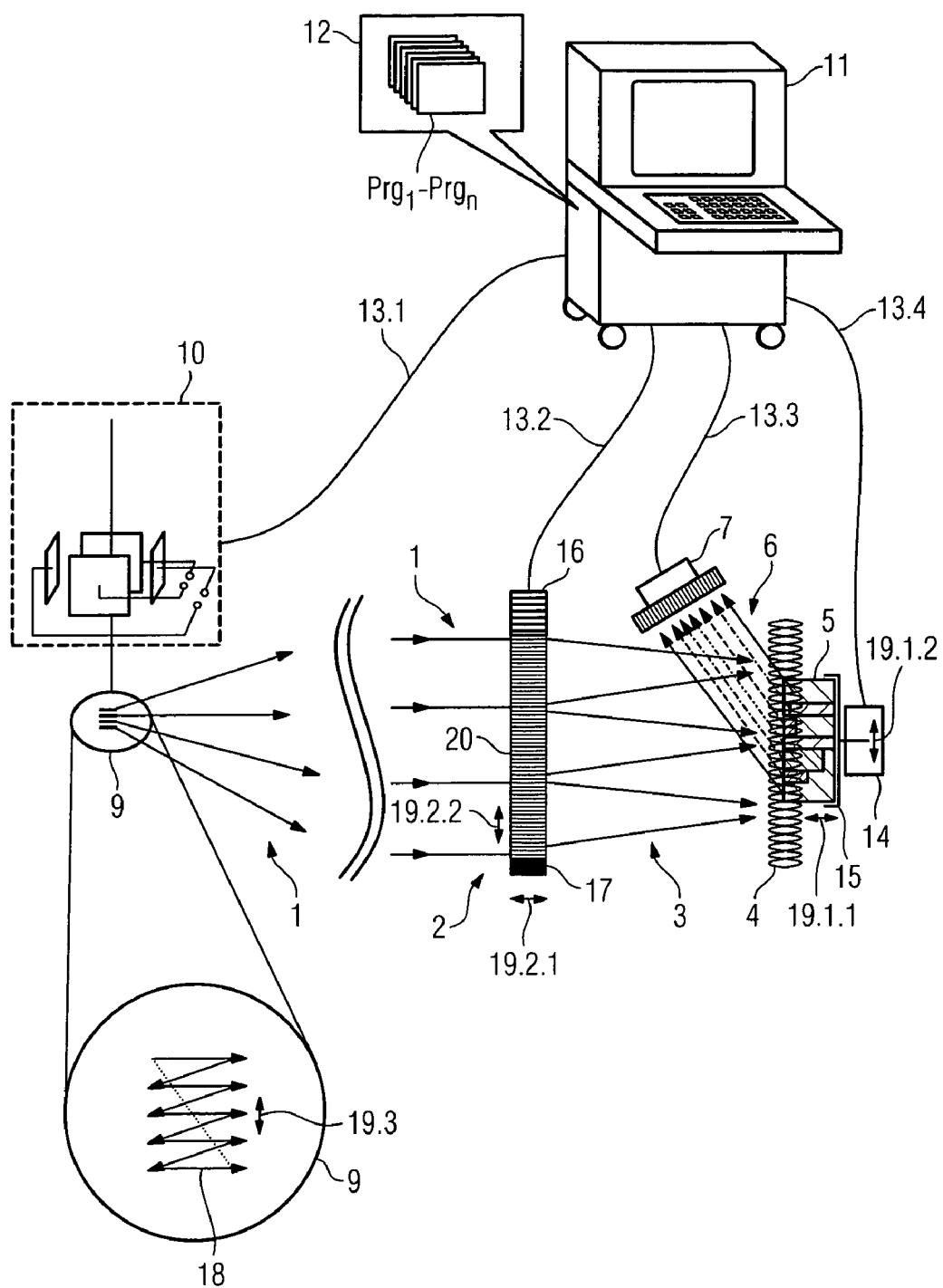
FIG. 3 shows a schematic of a measurement station with a measuring arrangement and control and evaluation computer.

FIG. 3 shows additionally a schematic of a measurement station with such a measuring arrangement in accordance with FIG. 1, there being connected to the measuring arrangement for the purpose of control and measurement evaluation a control and arithmetic unit 11 that contains in a memory 12 appropriate programs for control and evaluation. By way of example, the control and data lines 13.1 to 13.4 can be used to control the x-ray tube illustrated here, which comprises an anode 9 and electron beam deflection 10, the phase grating 2 and the movement apparatus 14 of the object holder 15.

Here, the anode 9 is operated with the aid of an electron beam that is moved like a grating over the anode surface such that there takes place at the scanned strip 18 an x-ray emission that emits a field with quasi-coherent x-ray beams 1.

Illustrated here as x-ray/optical grating 2 is a gas cell 20 that has an ultrasound generator 16 at one end and an ultrasound reflector 17 at the other end such that it is possible by appropriately controlling the ultrasound generator via the arithmetic and control unit 11 to generate in the gas cell 20 between the ultrasound generator 16 and the ultrasound reflector 17 a standing sound wave that leads to intensive density differences at periodic intervals and acts as a phase or absorption grating for the penetrating radiation. The examination object is located on an object holder 15 that can optionally move the examination object via a movement apparatus 14 in the desired spatial directions within the x-ray standing wave field 4.

The examination object can be nondestructively examined with reference to its inner structure with regard to the material distribution and the material itself by optionally moving the focal spot, which is formed like a grating, on the anode 9, and/or by displacing the entire phase grating 2 including a gas cell 20, with an ultrasound generator 16 and ultrasound reflector 17, and/or by electronically controlled displacement of the ultrasound standing wave field in the gas cell 20 functioning as phase grating, and/or of the examination object, and by measuring the different emitted radiation by the detector 7 with subsequent Fourier analysis of the results.

These movements are symbolized by arrows with the reference symbols 19.1.1, 19.1.2, 19.2.1, 19.2.2 and 19.3, it being possible for the examination object 5 to be moved both in the beam direction and transverse to the beam direction, as a result of which the standing wave field 4 is differently positioned in the examination object 5, while the focal spot strip 18 moves only transverse to the beam direction.

The proposed technique enables a nondestructive and non-scanning examination of an object in order to determine the elemental concentration distribution, which is able to detect all measurable elements with the aid of x-ray fluorescence spectroscopy. It is possible in this case to carry out a determination of the elemental distribution in up to three dimensions.

The described method can be applied both to the emitted x-ray fluorescence radiation and scattered radiation (Compton scattered radiation, Rayleigh scattered radiation), and to photoelectron radiation and Auger electron radiation. The spatially selective excitation is performed via an x-ray standing wave field in all variants of this technique.

When the object to be examined has elemental concentration distributions for which specific prior information is available, the requirements placed on the number of Fourier amplitudes to be determined can be reduced. For example, objects with periodic elemental concentration distributions require only a limited number of Fourier amplitudes for a perfect description.

It goes without saying that the above named features of the invention can be used not only in the respectively specified combination, but also in other combinations or on their own without departing from the scope of the invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for nondestructive analysis of an examination object, comprising:
   generating x-radiation, including a specific energy spectrum, via an x-ray source;
   generating, with the aid of at least one x-ray/optical grating in a beam path of the x-radiation, a standing wave field of the x-radiation positioned at least partially in the examination object, the x-ray source and the examination object being positioned on opposite sides of the at least one x-ray/optical grating and separate to the at least one x-ray /optical grating; and
   measuring the radiation excited by the x-ray standing wave field in the examination object as a function of at least one relative position between the examination object and the x-ray standing wave field, a material distribution in the examination object being inferred from the measurement result of the radiation excited by the x-ray standing wave field.

2. The method as claimed in claim 1, wherein an absorption grating is used as the x-ray/optical grating.

3. The method as claimed in claim 1, wherein, as the x-ray/optical grating, a phase grating is used that produces a phase shift by $\lambda/2$ for a portion of the x-rays.

4. The method as claimed in claim 1, wherein the total intensity of the radiation excited by the x-ray standing wave field is measured as a function of a relative position between the examination object and the x-ray standing wave field.

5. The method as claimed in claim 4, wherein an amplitude, a phase and a mean value of the excited radiation intensity with regard to a spatial frequency prescribed by the standing wave field are determined from an intensity profile.

6. The method as claimed in claim 5, wherein a Fourier analysis of the intensity profile is carried out.

7. The method as claimed in claim 6, wherein a spatial distribution of at least one specific material in the examination object is determined from the results of a number of Fourier analyses.

8. The method as claimed in claim 1, wherein a spectral intensity distribution of the radiation excited by the x-ray standing wave field is measured as a function of a relative position between the examination object and the x-ray standing wave field.

9. The method as claimed in claim 8, wherein an amplitude a phase and a mean value of an excited energy-specific radiation intensity with regard to a spatial frequency prescribed by a special standing wave field is determined from a spectral intensity profile.

10. The method as claimed in claim 9, wherein a Fourier analysis of the intensity profile is carried out.

11. The method as claimed in claim 10, wherein a spatial distribution of at least one specific material in the examination object is determined from the results of a number of Fourier analyses.

12. The method as claimed in claim 1, wherein different positions of the x-ray/optical grating relative to the examination object are used in order to produce different relative positions between the x-ray standing wave field and the examination object, and to measure the excited radiation.

13. The method as claimed in claim 1, wherein at least two different x-ray/optical gratings of different grating period that are inserted alternately for the purpose of measurement into the beam path are used in order to produce different relative positions between the x-ray standing wave field and the examination object and to measure the excited radiation.

14. The method as claimed in claim 1, wherein an x-ray/optical grating produced by ultrasound is used in order to produce different relative positions between the x-ray standing wave field and the examination object and to measure the excited radiation.

15. The method as claimed in claim 14, wherein standing waves of different periods are formed in the x-ray/optical grating produced by ultrasound.

16. A method comprising:
   carrying out the method of claim 1 for at least two different radiation energies of the exciting x-radiation.

17. The method as claimed in claim 16, wherein, for each radiation energy relative to which a standing wave field of the radiation is generated, a specific phase grating tuned to the energy is used.

18. The method as claimed in claim 16, wherein at least two phase gratings that are tuned to different radiation energies are used simultaneously in the beam path.

19. The method as claimed in claim 16, wherein use is made in the beam path of at least one phase grating that can be variably tuned to the radiation energy and whose tuning is set for each currently used radiation energy.

20. The method as claimed in claim 19, wherein the settable phase grating uses a standing ultrasound field and produces structural differences in a medium that correspond to a phase grating in alignment and grating period.

21. The method as claimed in claim 20, wherein a gas is used as medium for the ultrasound field.

22. The method as claimed in claim 20, wherein a liquid is used as medium for the ultrasound field.

23. The method as claimed in claim 20, wherein a suspension is used as medium for the ultrasound field.

24. The method as claimed in claim 20, wherein a solid is used as medium for the ultrasound field.

25. The method as claimed in claim 1, wherein use is made as radiation source of an x-ray tube with a punctiform focus relative to the distance from the x-ray/optical grating, such that the x-ray/optical grating sees largely coherent x-radiation.

26. The method as claimed in claim 1, wherein synchrotron radiation is used as coherent x-radiation.

27. The method as claimed in claim 1, wherein use is made as the radiation source of an x-ray tube having at least one absorption grating, arranged in the beam path downstream of a focus, in order to generate a field of quasi-coherent x-rays with a specific radiation energy.

28. The method as claimed in claim 1, wherein at least one detector is used in order to determine the radiation excited by the standing wave field in the examination object.

29. The method as claimed in claim 1, wherein a spectral distribution of the radiation excited by the standing wave field in the examination object is determined.

30. The method as claimed in claim 1, wherein at least one x-ray emission excited by the x-ray standing wave field is detected by the at least one detector.

31. The method as claimed in claim 1, wherein at least one electron emission excited by the x-ray standing wave field is detected by the at least one detector.

32. The method as claimed in claim 1, wherein the radiation emitted by the standing wave field in the examination object is measured one dimensionally as a function of the relative position of the standing wave field and the examination object.

33. The method as claimed in claim 1, wherein the radiation emitted by the standing wave field in the examination object is measured two dimensionally as a function of the relative position of standing wave field and examination object.

34. The method as claimed in claim 1, wherein the radiation emitted by the standing wave field in the examination object is measured three dimensionally as a function of the relative position of the standing wave field and the examination object.

35. A measuring arrangement for nondestructive analysis of an examination object, comprising:
- an x-ray source to generate x-radiation;
- at least one x-ray/optical grating, arranged in a beam path of the x-ray source to generate a standing wave field of the radiation that is partially positioned in the examination object, the x-ray source and the examination object being positioned on opposite sides of the at least one x-ray/optical grating and separate to the at least one x-ray /optical grating; and
- at least one detector, positioned outside the beam path of the x-ray source, to measure the radiation emitted by the standing wave field in the examination object as a function of the relative position between the examination object and the standing wave field.

36. The measuring arrangement as claimed in claim 35, wherein an arithmetic and control unit is provided to execute programs that simulate the method steps of
- generating x-radiation, including a specific energy spectrum, via an x-ray source;
- generating, with the aid of at least one x-ray/optical grating in the beam path of the x-radiation, a standing wave field of the x-radiation positioned at least partially in the examination object; and
- measuring the radiation excited by the x-ray standing wave field in the examination object as a function of at least one relative position between the examination object and the x-ray standing wave field, a material distribution in the examination object being inferred from the measurement result of the radiation excited by the x-ray standing wave field.

37. The measuring arrangement as claimed in claim 35, further comprising controllable drive means for relative positioning between the examination object and the standing wave field, configured to execute a movement of the examination object one dimensionally.

38. The measuring arrangement as claimed in 35, further comprising controllable drive means for relative positioning between the examination object and the standing wave field, configured to execute a movement of the examination object two dimensionally.

39. The measuring arrangement as claimed in 35, further comprising controllable drive means for relative positioning between the examination object and the standing wave field, configured to execute a movement of the examination object three dimensionally.

40. The measuring arrangement as claimed in claim 35, further comprising means for producing a relative position between examination object and standing wave field by way of a movement of the phase grating, at least with reference to its grating lines.

41. The method as claimed in claim 17, wherein at least two phase gratings that are tuned to different radiation energies are used simultaneously in the beam path.

42. The method as claimed in claim 20, wherein a piezo-electrically excitable solid is used as medium for the ultrasound field.

* * * * *